United States Patent
Oakley et al.

(10) Patent No.: US 10,912,888 B2
(45) Date of Patent: Feb. 9, 2021

(54) DRIVING CONFIGURATION FOR A DRUG DELIVERY DEVICE

(71) Applicant: Sanofi, Paris (FR)

(72) Inventors: Tom Oakley, Cambridge (GB); Stuart Milne, Buckden St. Neots (GB)

(73) Assignee: Sanofi, Paris (FR)

( * ) Notice: Subject to any disclaimer, the term of this patent is extended or adjusted under 35 U.S.C. 154(b) by 674 days.

(21) Appl. No.: 14/905,230

(22) PCT Filed: Jul. 17, 2014

(86) PCT No.: PCT/EP2014/065334
§ 371 (c)(1),
(2) Date: Jan. 14, 2016

(87) PCT Pub. No.: WO2015/007815
PCT Pub. Date: Jan. 22, 2015

(65) Prior Publication Data
US 2016/0175525 A1    Jun. 23, 2016

(30) Foreign Application Priority Data

Jul. 17, 2013 (EP) .................. 13176859

(51) Int. Cl.
*A61M 5/20* (2006.01)
*A61M 5/315* (2006.01)
*A61M 5/30* (2006.01)

(52) U.S. Cl.
CPC ............ *A61M 5/2033* (2013.01); *A61M 5/20* (2013.01); *A61M 5/30* (2013.01); *A61M 5/3155* (2013.01);
(Continued)

(58) Field of Classification Search
CPC ........ A61M 5/20; A61M 5/2033; A61M 5/30; A61M 5/31533; A61M 5/31548;
(Continued)

(56) References Cited

U.S. PATENT DOCUMENTS 2,902,994 A * 9/1959 Scherer ............... A61M 5/30 604/68
4,064,879 A * 12/1977 Leibinsohn ........... A61M 5/486 604/121
(Continued)

FOREIGN PATENT DOCUMENTS

| JP | H08/511460 | 12/1996 |
|---|---|---|
| WO | WO 95/00193 | 1/1995 |

(Continued)

OTHER PUBLICATIONS

Rote Liste, "50. Hypophysen-, Hypothalamushormone, andere regulatorische Peptide u. ihre Hemmstofe," Chapter 50, ed. 2008, 20 pages.
(Continued)

*Primary Examiner* — Quynh-Nhu H. Vu
(74) *Attorney, Agent, or Firm* — Fish & Richardson P.C.

(57) ABSTRACT

The driving configuration for a drug delivery device comprises an energy storing member (2) providing a force suitable for driving a bung (1) arranged in a container (3), the bung being movable relative to the container. The energy storing member (2) is loaded by an alteration of its mechanical state with respect to a mounting element (5), which is relocatable in such a manner that a force provided by the energy storing member when it is loaded is reduced by a relocation of the mounting element.

18 Claims, 1 Drawing Sheet

(52) U.S. Cl.
CPC .... *A61M 5/31533* (2013.01); *A61M 5/31548* (2013.01)

(58) Field of Classification Search
CPC .......... A61M 5/3155; A61M 2005/202; A61M 5/2026; A61M 5/31525
See application file for complete search history.

(56) References Cited

U.S. PATENT DOCUMENTS

| | | | | |
|---|---|---|---|---|
| 5,176,642 | A * | 1/1993 | Clement | A61M 1/0062 604/135 |
| 5,270,685 | A * | 12/1993 | Hagen | A61M 5/486 128/DIG. 12 |
| 5,485,853 | A * | 1/1996 | Stubbs | A61B 10/0045 600/565 |
| 5,697,917 | A * | 12/1997 | Sadowski | A61M 5/30 604/218 |
| 5,800,405 | A * | 9/1998 | McPhee | A61M 5/1454 604/135 |
| 6,475,193 | B1 * | 11/2002 | Park | A61M 5/204 604/191 |
| 7,207,951 | B1 * | 4/2007 | Lurie | A61B 10/0045 600/578 |
| 9,707,335 | B2 * | 7/2017 | Agard | A61M 5/14216 |
| 2007/0065319 | A1 * | 3/2007 | Hommann | A61M 5/31583 417/477.1 |
| 2007/0191762 | A1 * | 8/2007 | Quinn | A61M 5/30 604/68 |
| 2008/0221531 | A1 * | 9/2008 | Alheidt | A61M 5/31511 604/236 |
| 2009/0163867 | A1 * | 6/2009 | Marshall | A61M 5/31586 604/136 |
| 2009/0177156 | A1 * | 7/2009 | MacLean | A61M 5/3155 604/135 |
| 2011/0009830 | A1 * | 1/2011 | Kosinski | A61M 5/31511 604/227 |
| 2013/0218093 | A1 * | 8/2013 | Markussen | A61M 5/2033 604/198 |
| 2015/0209505 | A1 * | 7/2015 | Hanson | A61M 5/14566 604/135 |
| 2016/0317738 | A1 * | 11/2016 | Cross | A61M 5/16881 |
| 2017/0361015 | A1 * | 12/2017 | McCullough | A61M 5/00 |

FOREIGN PATENT DOCUMENTS

| | | |
|---|---|---|
| WO | WO 97/31665 | 9/1997 |
| WO | WO 2004/006998 | 1/2004 |
| WO | WO 2012/072568 | 6/2012 |
| WO | WO 2013/083715 | 6/2013 |

OTHER PUBLICATIONS

International Search Report and Written Opinion in International Application No. PCT/EP2014/065334, dated Sep. 26, 2014, 9 pages.
International Preliminary Report on Patentability in International Application No. PCT/EP2014/065334, dated Jan. 19, 2016, 6 pages.

* cited by examiner

DRIVING CONFIGURATION FOR A DRUG DELIVERY DEVICE

CROSS-REFERENCE TO RELATED APPLICATIONS

This application is a U.S. national stage application under 35 USC § 371 of International Application No. PCT/EP2014/065334, filed on Jul. 17, 2014, which claims priority to European Patent Application No. 13176859.0, filed on Jul. 17, 2013, the entire contents of which are incorporated herein by reference.

Drug delivery devices, in particular pen-type injection devices, comprise a bung, which serves to eject doses of a drug from a container like a drug cartridge and may be provided as part of a drug cartridge. The bung is usually driven by a piston rod, which may be provided with a mechanism for setting a dose and for advancing the piston rod to deliver the dose set. If the bung remains in the same position for some time, typically for more than twenty-four hours, the bung may form bonds to the cartridge, so that it sticks to the cartridge and an increased force is required to move the bung from its resting position. This may especially be the case for an elastomeric bung placed in a cartridge made from glass or thermoplastic. As an example, the force can increase from 15 N for a recently-moved bung to 30 N for a bung that has not been recently moved. This increase in force required to move the bung is typical after the storage period between manufacture and first use.

In spring-driven pen injectors the driving force to move the bung is provided by a spring, which may be a torsion spring. The spring must provide enough torque to overcome the static friction or 'stiction' force, even when the user sets only the minimum dose to be delivered. Therefore, a spring that can provide enough force to overcome the stiction force might be used. The disadvantages of using a higher-force spring are that the spring may need to be larger, leading to a larger device size and mass and higher device cost. Furthermore the user must apply more torque to select a dose than would otherwise be necessary, and the increased forces on components mean that higher strength materials or component design must be used to avoid failures due to deflection, yield or creep.

It is an object of the present invention to provide an easy way to overcome a stiction of the bung of a drug delivery device to a drug container like a cartridge.

This object is achieved with the driving configuration according to claim 1 and with the drug delivery device according to claim 8. Further embodiments and variants derive from the dependent claims.

An energy storing member according to this invention shall mean any member or component that is suitable to be loaded by storing mechanical energy in order to be able to provide a force driving a bung of a drug delivery device. The energy storing member may particularly be a spring, especially a compression spring, a tension spring, a torsion spring, a leaf spring or a sheet spring, for instance, or it may be a component containing a compressed gas of variable pressure, for example.

The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39), des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence des Pro36 Exendin-4(1-39)-Lys6-NH2 (AVE0010), H-(Lys)6-des Pro36 [Asp28] Exendin-4(1-39)-Lys6-NH2, des Asp28 Pro36, Pro37, Pro38Exendin-4(1-39)-NH2, H-(Lys)6-des Pro36, Pro38 [Asp28] Exendin-4(1-39)-NH2, H-Asn-(Glu)5des Pro36, Pro37, Pro38 [Asp28] Exendin-4 (1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4 (1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4 (1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(02)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2) 25, Asp28] Exendin-4(1-39)-5 NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2) 25, Asp28] Exendin-4(1-39)-10 (Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, β, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

In one aspect the invention relates to a driving configuration for a drug delivery device comprising an energy storing member providing a force suitable for driving a bung in a container. The energy storing member is loaded by an alteration of its mechanical state with respect to a mounting element, which is relocatable, in particular relocatable with respect to the container, to a housing or to some other element of reference, in such a manner that a force provided by the energy storing member when it is loaded is reduced by a relocation of the mounting element. The result of the relocation of the mounting element is that the preload on the energy storing member is lower for every use of the device, particularly for every injection, after the first use. The larger preload that is effected before the first use increases the force moving a bung in a cartridge and thus compensates for a stiction force that is typically present after the storage period between manufacture and first use. After the first use, the effected preload is decreased by the relocation of the mounting element, and the torque required to set a further dose is not larger than it is necessary when the initial stiction has been removed. This has the advantage that no elevated torque to set a dose has to be applied after the first use.

An embodiment of the driving configuration further comprises an operation element provided for the relocation of the mounting element. The operation element has the advantage that it enables to modify the operation of the mechanism either automatically or manually by a user in order to provide the desired decrease of the preload.

In a further embodiment the operation element is adapted to produce the relocation of the mounting element by a shift of the operation element relative to the mounting element. This embodiment has the advantage that the relocation of the mounting element can be effected by a further mechanical operation that is adapted to the general operation of the mechanism.

In a further embodiment the operation element is arranged to be operable by the user. This embodiment has the advantage that the user is enabled to relocate the mounting element whenever they desire to reduce the preload.

In a further embodiment the mounting element is provided for a relocation during a first release of energy stored in the energy storing member. This embodiment has the advantage that the preload will already be reduced for a second use of the device and the relocation of the mounting element can be performed automatically.

In a further embodiment the mounting element is provided for a relocation after a first release of energy stored in the energy storing member and before the energy storing member is loaded again. This embodiment has the advantage that the preload will already be reduced for a second use of the device and the relocation of the mounting element can be performed automatically or manually.

In a further embodiment the force provided by the energy storing member is adapted to overcome a stiction between the bung and the container before the relocation of the mounting element. This embodiment has the advantage that the force driving the bung in the first use of the device is sufficiently strong even if there is a stiction force due to the storage interval between the manufacture and the first use.

In a further embodiment the mounting element relocates the energy storing member relative to the piston rod and/or the bung and/or the container, which may be a cartridge containing the drug, for instance. This embodiment has the advantage that a portion of the energy storing member can be fixed relative to other members or elements, for example the housing.

In another aspect the invention relates to a drug delivery device comprising such a driving configuration and further a container containing a medicament with a bung located in the container. The drug delivery device may especially be an injection device and/or a pen-type device. This drug delivery device has the advantage that a larger preload of the energy storing member is effected before the first use, so that the increased force moving the bung compensates for a stiction, and no elevated torque for setting a dose has to be applied after the first use.

In an embodiment of the drug delivery device, the mounting element relocates the energy storing member relative to the bung and/or relative to the container.

The following is a detailed description of embodiments of the driving configuration in conjunction with the appended drawings.

Figure 1:
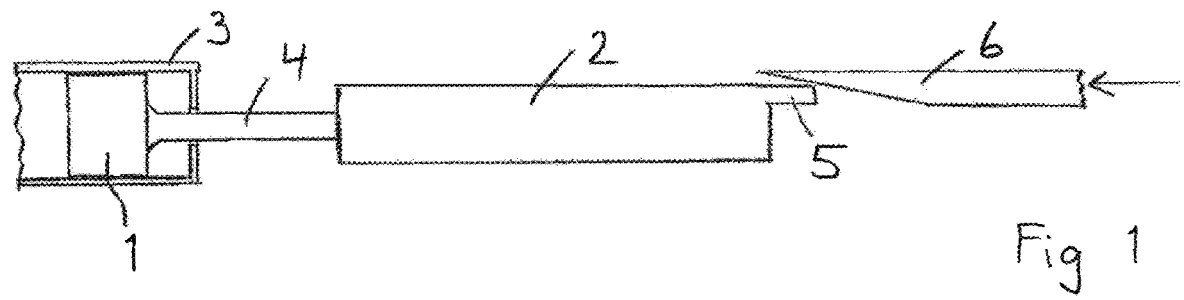
FIG. 1 is a schematic cross section of an embodiment of the driving configuration.

FIG. 1 shows a driving configuration including an arrangement of a bung 1, an energy storing member 2 comprising a relocatable mounting element 5, and an operation element 6. The energy storing member 2 is loaded by an alteration of its mechanical state with respect to the mounting element 5. The bung 1 is arranged in a container 3, which may be a drug cartridge 3, and may be advanced by a piston rod 4 driven by a force provided by the energy storing member 2. The mounting element 5 is initially arranged in a position relative to the container 3 in such a manner that the energy storing member 2 is loaded to generate a force that is suitable to overcome a possible stiction between the bung 1 and the container 3. The operation element 6 is provided to relocate the mounting element 5 and is operated in conjunction with an advancement of the bung 1, either by starting the delivery of the drug or during the movement of the bung 1 or after the delivery of a dose of the drug. The shape of the operation element 6 may be adapted for this purpose. It may especially be tapered or provided with a surface structure that engages the mounting element 5. A shift of the operation element 6 in the direction of the arrow shown in FIG. 1, for example, may then relocate the mounting element 5 in the desired way. When the mounting element 5 is relocated, a capacity of the energy storing member 2 is reduced in a predefined way. A driving force provided by the energy storing member 2, when it is in a loaded state, is thus reduced.

In drug delivery devices that are driven by a spring, especially in pen-type injectors, a spring provides the energy storing member 2. One end of the spring is essentially fixed relative to another component, particularly to a main body, of the device, and the fixed end of the spring corresponds to the relocatable mounting element. Even if this end moves due to tolerances or because it mates with a movable component, a movement of the spring relative to the component of reference is effectively negligible. When the spring is loaded by a user or when the stored energy is released, the opposite end of the spring is moved relative to the fixed end. In the case of a torsion spring it is rotated relative to the fixed end. A preload of the spring is favourable to make the torque less dependent on the progress of the release of the spring and therefore the applied force more consistent throughout a drug delivery.

A drug delivery is usually started by moving an element or component of the drug delivery device, typically a button, which releases the opposite end of the spring and allows the spring to drive the mechanism to deliver the dose. Before the first drug delivery, the spring is sufficiently preloaded to be able to generate a force that suffices to drive the bung, even if some stiction has to be overcome and only the minimum dose volume is set. At some time after the start of the first drug delivery, typically when the first drug delivery has been finished, for example, the fixed but relocatable end of the spring is caused to move to a new position relative to other components. The result of this relocation is that the preload of the spring will be lower for every subsequent use of the drug delivery device.

The operation of the button used to start a drug delivery can be coupled with an operation causing the relocation of the mounting element 5. The operation of the button may directly move a member like the operation element 6 shown in FIG. 1, for example, or the first release of energy stored in the spring may be used to relocate the mounting element 5. The energy need not be stored by a spring. For example, the energy could instead be stored in a compressed gas, for which the nominal pressure is increased or decreased after the first device use.

A high spring preload is only required for the first drug delivery, because it is only the first drug delivery which must overcome the high force required to move the bung 1 after an extended rest period. During the normal use of the device, the bung 1 does not tend to have enough time to stick to the container 3 with such a high stiction force. Advantages of reducing the spring preload after first use are that less input force or torque applied by the user is required to set a dose, and that components receive less load and so deflection, yield and creep issues are reduced. As a result, some components can be smaller, simpler or made from cheaper materials due to the reduced forces in normal use.

Figure 2:
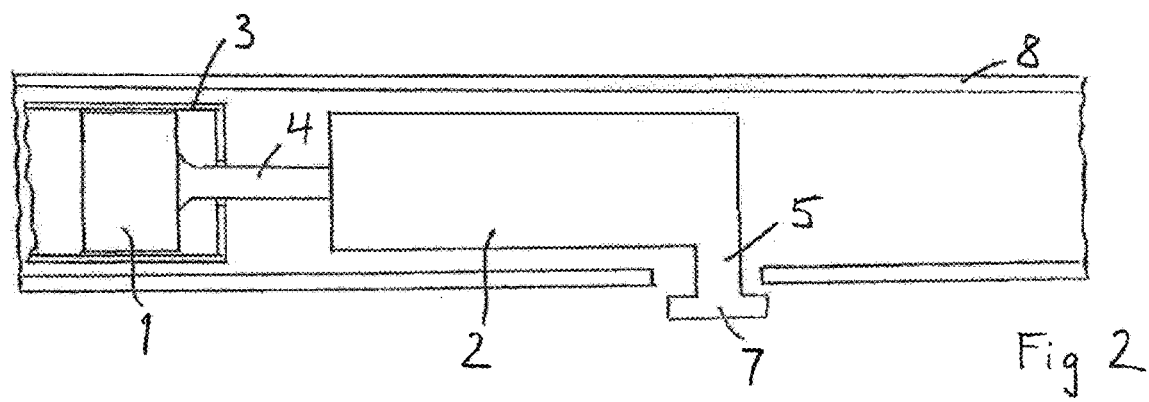
FIG. 2 is a schematic cross section of a further embodiment of the driving configuration.

FIG. 2 is a schematic cross section of a further embodiment of the driving configuration. The elements of the embodiment according to FIG. 2 that are similar to elements of the embodiment according to FIG. 1 are designated with the same reference numerals. In the embodiment according to FIG. 2 the energy storing member 2 is provided with a mounting element 5 that can be relocated by the user by means of a further operation element 7, which is arranged to be operable by the user. The operation element 7 may extend from a body or housing 8 of the drug delivery device, for example. The operation element 7 can be provided to relocate the mounting element 5 directly or to change the arrangement of the energy storing member 2 within the driving configuration in such a manner that the mounting element 5 is relocated to a position which causes the energy storing member 2 to be loaded less than before by the same operation steps performed by the user.

Figure 3:
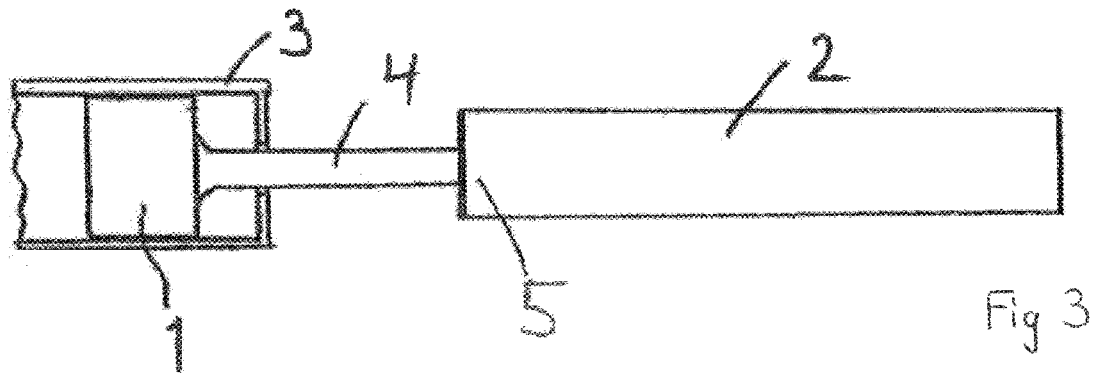
FIG. 3 is a schematic cross section of a further embodiment of the driving configuration.

FIG. 3 is a schematic cross section of a further embodiment of the driving configuration. The elements of the embodiment according to FIG. 3 that are similar to elements of the embodiment according to FIG. 1 are designated with the same reference numerals. In the embodiment according to FIG. 3, the energy storing member 2 is provided with a mounting element 5 that can be relocated relative to the piston rod 4 and/or the bung 1 and/or the cartridge 3. The relocation serves to reduce load applied to, and provided by, the energy storing element 2 for dose setting and drug delivery after relocation. Therefore, less force or torque is require from the user during dose setting, and some components can be smaller, simpler or made from cheaper materials due to the reduced forces in normal use.

In any configuration, the relocation of the energy storing member 2 could occur before, on commencement of, during, at completion of, or after drug delivery.

REFERENCE NUMERALS 1 bung
2 energy storing member
3 container
4 piston rod
5 relocatable element
6 operation element
7 operation element
8 housing

The invention claimed is:

1. A drive mechanism for a drug delivery device, the drive mechanism comprising:
 a spring configured to provide a force to drive a bung into a drug container; and
 a mounting element on a first end of the spring, wherein the mounting element is movable from a first position into a second position, wherein the mounting element is configured to be in the first position before a first use of the drug delivery device and to be in the second position for every use after the first use of the drug delivery device,
 wherein, both when the mounting element is in the first position and when the mounting element is in the second position, the spring is configured to be loaded by movement of a second end of the spring relative to the mounting element to set a dose of a drug and to be released to allow the second end of the spring to drive the bung into the drug container for drug delivery of the set dose of the drug, wherein the mounting element and the spring are configured such that, for setting a same dose, a force for loading the spring when the mounting element is in the second position is smaller than a force for loading the spring when the mounting element is in the first position.

2. The drive mechanism according to claim 1, further comprising:
an operation element operable to cause movement of the mounting element from the first position into the second position.

3. The drive mechanism according to claim 2, wherein the operation element is adapted to cause the movement of the mounting element by a shift of the operation element relative to the mounting element.

4. The drive mechanism according to claim 2, wherein the operation element is arranged to be operable by a user.

5. The drive mechanism according to claim 1, wherein the force provided by the spring when the mounting element is in the first position is adapted to overcome a stiction between the bung and the drug container before movement of the mounting element from the first position to the second position.

6. The drive mechanism according to claim 1, wherein a result of movement of the mounting element from the first position to the second position is that a preload on the spring is lower for every injection after the first use of the drug delivery device.

7. The drive mechanism according to claim 1, wherein the mounting element is configured to be in the first position during dose setting for the first use of the drug delivery device.

8. The drive mechanism according to claim 7, wherein the mounting element is configured to be in the second position during dose setting for a second use of the drug delivery device.

9. The drive mechanism according to claim 1, wherein the spring is a torsion spring.

10. The drug delivery device according to claim 9, wherein the drug delivery device is a pen-type device.

11. The drive mechanism according to claim 1,
wherein the spring is a torsion spring, and
wherein the mounting element and the spring are configured such that, for setting the same dose, a torque for loading the spring in the second position is smaller than a torque for loading the spring in the first position.

12. The drug delivery device according to claim 11, wherein the second end of the torsion spring is configured to be rotated relative to the first end of the torsion spring when the torsion spring is loaded by a user and when stored energy of the torsion spring is released.

13. The drug delivery device according to claim 12, wherein the drug delivery device is a pen-type device.

14. A drug delivery device comprising:
a drug container containing a medicament and a bung located in the drug container; and
a drive mechanism comprising:
a spring configured to provide a force to drive the bung into the drug container; and
a mounting element on a first end of the spring, wherein the mounting element is movable from a first position into a second position, wherein the mounting element is configured to be in the first position before a first use of the drug delivery device and to be in the second position for every use after the first use of the drug delivery device,
wherein, both when the mounting element is in the first position and when the mounting element is in the second position, the spring is configured to be loaded by movement a second end of the spring relative to the mounting element to set a dose of a drug and to be released to allow the second end of the spring to drive the bung into the drug container for drug delivery of the set dose of the drug,
wherein the mounting element and the spring are configured such that, for setting a same dose, a force or loading the spring when the mounting element is n the second position is smaller than a force for loading the spring when the mounting element is in the first position.

15. The drug delivery device according to claim 14, wherein the drug delivery device is an injection device.

16. The drug delivery device according to claim 14, wherein the drug delivery device is a pen-type device.

17. The drug delivery device according to claim 14, wherein the mounting element is movable to relocate the first end of the spring relative to the bung and/or relative to the drug container.

18. The drug delivery device according to claim 14, wherein a result of movement of the mounting element from the first position to the second position is that a preload on the spring is lower for every injection after the first use of the drug delivery device.

* * * * *

UNITED STATES PATENT AND TRADEMARK OFFICE
CERTIFICATE OF CORRECTION

PATENT NO. : 10,912,888 B2
APPLICATION NO. : 14/905230
DATED : February 9, 2021
INVENTOR(S) : Tom Oakley and Stuart Milne Page 1 of 1

It is certified that error appears in the above-identified patent and that said Letters Patent is hereby corrected as shown below:

On the Title Page

In Column 2 (Item (56) Other Publications), Line 2, delete "Hemmstofe,"" and insert
-- Hemmstoffe," --

In the Claims

In Column 10, Line 25 (approx.), Claim 14, after "movement" insert -- of --

In Column 10, Line 32 (approx.), Claim 14, delete "or" and insert -- for --

In Column 10, Line 33 (approx.), Claim 14, delete "n" and insert -- in --

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*